(12) United States Patent
Plank et al.

(10) Patent No.: US 6,767,109 B2
(45) Date of Patent: Jul. 27, 2004

(54) LIGHT HARDENING DEVICE AND A LIGHT SOURCE SUITABLE FOR USE IN A LIGHT HARDENING DEVICE

(75) Inventors: Wolfgang Plank, Rankweil (AT); Gottfried Rohner, Altstatten (CH); Thomas Stahl, Dauchingen (DE)

(73) Assignee: Ivoclar Vivadent AG, Schaon (LI)

( * ) Notice: Subject to any disclaimer, the term of this patent is extended or adjusted under 35 U.S.C. 154(b) by 0 days.

(21) Appl. No.: 10/177,014

(22) Filed: Jun. 20, 2002

(65) Prior Publication Data

US 2002/0186558 A1 Dec. 12, 2002

Related U.S. Application Data

(60) Provisional application No. 60/308,681, filed on Jul. 30, 2001.

(30) Foreign Application Priority Data

Jun. 6, 2001 (DE) .......................... 101 27 416

(51) Int. Cl.[7] .............................................. A61C 13/15
(52) U.S. Cl. ...................... 362/119; 362/119; 362/800; 433/29
(58) Field of Search ................................ 362/109, 119, 362/202, 230, 231, 234, 294, 373, 800, 572, 577, 249; 433/29; 313/318.05, 556

(56) References Cited

U.S. PATENT DOCUMENTS

| 4,298,806 A | * | 11/1981 | Herold .................... 250/504 H |
| 5,420,768 A |   | 5/1995  | Kennedy |
| 5,634,711 A |   | 6/1997  | Kennedy et al. |
| 5,912,470 A | * | 6/1999  | Eibofner et al. ......... 250/504 H |
| 5,975,895 A | * | 11/1999 | Sullivan ...................... 433/29 |
| 6,123,545 A | * | 9/2000  | Eggler et al. ................. 433/29 |
| 6,200,134 B1 | * | 3/2001 | Kovac et al. ................. 433/29 |
| 6,318,996 B1 |   | 11/2001 | Melikechi et al. |
| 6,439,888 B1 | * | 8/2002 | Boutoussov et al. ......... 433/215 |

FOREIGN PATENT DOCUMENTS

| DE | 295 11 927 U1 | 2/1997 |
| DE | 196 19 154 A1 | 6/1997 |
| DE | 198 10 573    | 9/1999 |
| DE | 19943393 C1 * | 9/1999 |
| EP | 1138276 A1 *  | 10/2001 |
| WO | WO 97/36552   | 10/1997 |
| WO | WO 00/13608   | 3/2000 |

* cited by examiner

*Primary Examiner*—Thomas M. Sember
*Assistant Examiner*—Hargobing S. Sawhney
(74) *Attorney, Agent, or Firm*—John C. Thompson; Alan S. Korman

(57) ABSTRACT

A light hardening device is provided and includes a light source having a plurality of LEDs supplied by an electrical energy source, and a cooling device arranged upstream of the light source and operable to cool the light hardening device. The LED arrangement is disposed on a rear surface of a cooling body and the light hardening device has a connection in the manner of a halogen glow lamp. Also, a light source is provided having a plurality of LEDs, a cooling body on which the LEDs are mounted, and a connector element and an overall exterior geometry, each of which corresponds to the respective connector element and overall exterior geometry of a conventional reflecting halogen glow lamp having a rated voltage of 12 volts.

19 Claims, 2 Drawing Sheets

LIGHT HARDENING DEVICE AND A LIGHT SOURCE SUITABLE FOR USE IN A LIGHT HARDENING DEVICE

CROSS-REFERENCE TO RELATED APPLICATIONS

This application claims foreign priority benefits under 35 U.S.C. §119(a)–(d) from German patent application ser. no. 101 27 416.5 filed Jun. 6, 2001. In addition, this application claims the benefit under 35 U.S.C. §119(e) of U.S. provisional patent application ser. No. 60/308,681 filed Jul. 30, 2001.

BACKGROUND OF THE INVENTION

The present invention relates to a light hardening device and a light source suitable for use in a light hardening device.

A conventional light hardening device is disclosed, for example, in U.S. Pat. No. 5,420,768. This conventional device includes a plurality of light diodes mounted on a common base body. The light emitted by the light diodes is conducted to a light guide and can be used, for example, for the light hardening of suitable polymerizable masses which are deployed, for example, in the dental practice.

It is further conventionally known to provide a cooling arrangement for the base body on which the light diodes are mounted.

It has already been proposed to use a cooling body as the base body, whereby, for example, reference is made to copending U.S. patent application Ser. No. 10/023,232. In accordance with the arrangement disclosed therein, a cooling body is provided which has numerous LEDs mounted on its base surface. The cooling body is encircled by ribbed elements and the light passing therefrom is conducted to a light guide, whereby a portion of the light exits after first being reflected by the ribbed elements which are arranged in front of the light guide and configured in opposition thereto.

The just described arrangement offers a basic good cooling of the LED arrangement.

To be sure, if for the purpose of achieving a maximum light output, the base surface of the cooling body is provided with a plurality of closely adjacent LED chips, then the cooling body becomes too hot in connection with an intensive outer cooling as a consequence of which, in accordance with the heretofore described conventional arrangement, a pre-determined distance between the LED chips must be maintained. The free surface surrounded by the chips serves at the same time as a reflective surface which reflects the light again which has been reflected from the mirrored inner counter cone (which has a geometry corresponding to that of the front ribbed element body) and the light is ultimately guided to the light guide.

U.S. Pat. No. 6,123,545 shows a device for curing polymerizable dental materials. In this device a conventional halogen lamp is employed.

This conventional approach has led, surprisingly, to the circumstance that exactly at the front ribbed element body, the ribbed element body is substantially heated so that, in fact, a water cooling arrangement has been proposed. A water cooling arrangement can, indeed, substantially improve the cooling effect, but such an arrangement increases the weight of the light hardening device to an extent that the device is too heavy for suitable hand deployment.

SUMMARY OF THE INVENTION

The present invention offers a solution to the challenge of providing a light hardening device as well as a light source which improves the light working efficiency —that is, the relationship or ratio between the light performance given thereby and the heat or warmth given off by the device.

The arrangement of the present invention offers, surprisingly, the possibility to improve the efficiency of the device despite a reduction in the base surface which is available for receiving thereon the LED chips. By the arrangement of the LED chips on the rear surface, the light guide is disposed in direct neighboring relationship thereto and the light can be irradiated thereunto by the LED chips. The cooling body preferably expands from the rear surface outwardly towards its other end so that the mass and surface available for heat transfer is, in comparison to the cross-section of the rear surface, drastically enlarged. In accordance with the present invention, it is particularly advantageous that, through the arrangement of the LED-chips on the rear surface —that is, immediately neighboring the light guide —there is not a need to provide reflective surfaces. In the known approaches in which the LED chips are mounted on the cooling body, the light is, to a large extent, conducted onto reflective surfaces, is reflected thereby, and, after varying multiple further reflections, eventually is guided to the light guide. Evaluations in connection with the understanding of the conventional approaches have shown that the reflecting activity not only reduces the light efficiency, but also increases considerably the heat or warmth which is generated and which must then necessarily be transferred or guided away.

In accordance with the present invention, it is provided, in contrast, to directly irradiate the light guide in a reflection free manner. The heat shed or given off by the LED chips is at the same time also emitted onto the light guide so that, in accordance with the present invention, the heat radiation can be deployed for polymerizable masses as well.

In accordance with the present invention, it is provided that the multiple LED arrangement gives off heat in the manner of a "hotter mark" approach to the light hardening apparatus. Through the distribution of heat over the relatively large surface area of the conically shaped cooling body, it is ensured that the light hardening device of the present invention is, in total, not heated too severely.

Additionally, the light hardening device of the present invention, in offering a particularly high light output, makes possible a rapid true hardening of the hardenable mass. The hardening time can be reduced, for example in contrast to that of a hand deployable halogen glow lamp, by one-half. By means of the shortened hardening time, the heat capacity of the cooling body also plays a role, on the other hand, to effect a reduction in the temperature level. This means, in practical use, that during the hardening time the increase in temperature exteriorly of the light hardening device is not noticeable and that the cooling apparatus undertakes, as well, a cooling function following the conclusion of the hardening process so that the temperature, when regarded over time, is graduated or smoothed.

In accordance with the present invention, it is nonetheless particularly advantageous that the LED arrangement in combination with the cooling body can be deployed, as well, in substitution for the reflecting halogen glow lamp of a hand deployed light hardening device. The device of the present invention permits a substantial increase in the light performance or output and the life or length of operation of the device and, thereby, as well, the reliability of the light hardening device is automatically increased. It is now possible to avoid the heretofore problematic hardening process which could be interrupted by the burning through of a glow lamp creating a situation in which patients having a partially hardened filling or the like have had to wait. Heretofore, in order to avoid such unfavorable situations in which a further hardening of a partially hardened filling or other dental restoration piece is no longer possible, it has been necessary to deploy two light hardening devices in the dental practice so that, in the event of a failure of the first light hardening device or the reaching of the end of its operational availability, the second light hardening device could be deployed. In accordance with the present invention, the need to deploy two light hardening devices is now eliminated in that the LED arrangement has a drastically increased life cycle and a complete failure or falling out is, in practice, completely foreclosed. The reason for this lies in the fact that the multiple arrangement of LED chips ensures that if a single chip falls out or fails, the light output or performance is reduced by, for example, 5% and this reduction in light output can be compensated for by an increased hardening time.

It is to be understood that the number of LED chips can be accommodated to a wide range of requirements. In connection with round socket elements for the light guide rod, an arrangement of 5×5 LED chips, for example, can be specified so that, in total, 25 chips are available or the corners chips can be omitted so that in total 21 chips are available. Preferably, the chips are arranged in the closest possible arrangement with one another and in immediate neighboring proximity to the entry of the light guide rod.

In accordance with the present invention, it is particularly advantageous that commercially available light guide devices need no further modification to be deployed as a light hardening apparatus or device in connection with the present invention, or to be provided with the light source of the present invention in substitution for the reflecting halogen glow lamp. In this manner, the cooling body preferably includes two electric contact rods or plug elements on its back end which correspond to the contact rods of a halogen glow lamp. The cooling process follows in the manner of a conventional halogen glow lamp cooling process by contact with the ribbed element bodies which encircle the halogen glow lamp. Preferably, the two ribbed element bodies are so firmly connected to one another as to ensure a secure arrangement so that the shedding or conducting away of the heat or warmth is assured.

Additionally, if a water cooling arrangement of the ribbed element bodies is to be factored in, so that the ribs are arranged in an overlapping aligned manner, it is preferable that an air cooling arrangement with a forced air element is provided which can thus lead to weight saving advantages.

It is additionally particularly advantageous that the temperature management of a commercially available light hardening device can be further used without modification. Typically, a forced air element or component is actuated as soon as the temperature exceeds a predetermined threshold value. Due to the improved working efficiency of the light source of the present invention, a reduced heat or thermal buildup occurs so that there is a corresponding prolongation of the time until the forced air element must be actuated.

The light hardening device and light source of the present invention are suitable as well for main voltage supply as well as for supply by means of a battery. Due to the substantially high working efficiency of the device for the light source, the life of the battery is extended.

In accordance with the present invention, it is particularly advantageous if the LED arrangement of chips is comprised of at least two different types of chips whose emission maximum are at different wave lengths. In this connection, the particular features of a two catalyzer system can be taken into account.

In an advantageous embodiment of the light hardening device of the present invention, it is further provided that the cooling body is configured in a hollow fashion and a control device is disposed in the interior of the cooling device for receiving thereon the LED chips. By a corresponding modification of the software or, alternatively, the hardware, of a hand device, it is also possible to sequentially actuate the two LED chip portions even if only two energy supply contacts are provided. In this connection, an impulse control can, for example, be provided, which is integrated with the control device disposed in the cooling body.

It is to be understood that any suitable desired modifications of the light hardening device or light source of the present invention are possible without going beyond the scope of the present invention. Thus, the cooling body can, as needed, also be configured as the base cooling body which can be connectable via corresponding adapters with the ribbed element bodies to ensure a good conducting away of the heat. It is also possible to improve the resistance to heat transfer between the cooling body and the ribbed element body by insertion of a conventional heat conducting paste.

BRIEF DESCRIPTION OF THE DRAWINGS

The object and advantages of the present invention will appear more clearly from the following specification in conjunction with the accompanying drawings, in which.

DETAILED DESCRIPTION OF THE PREFERRED EMBODIMENT

Figure 1:
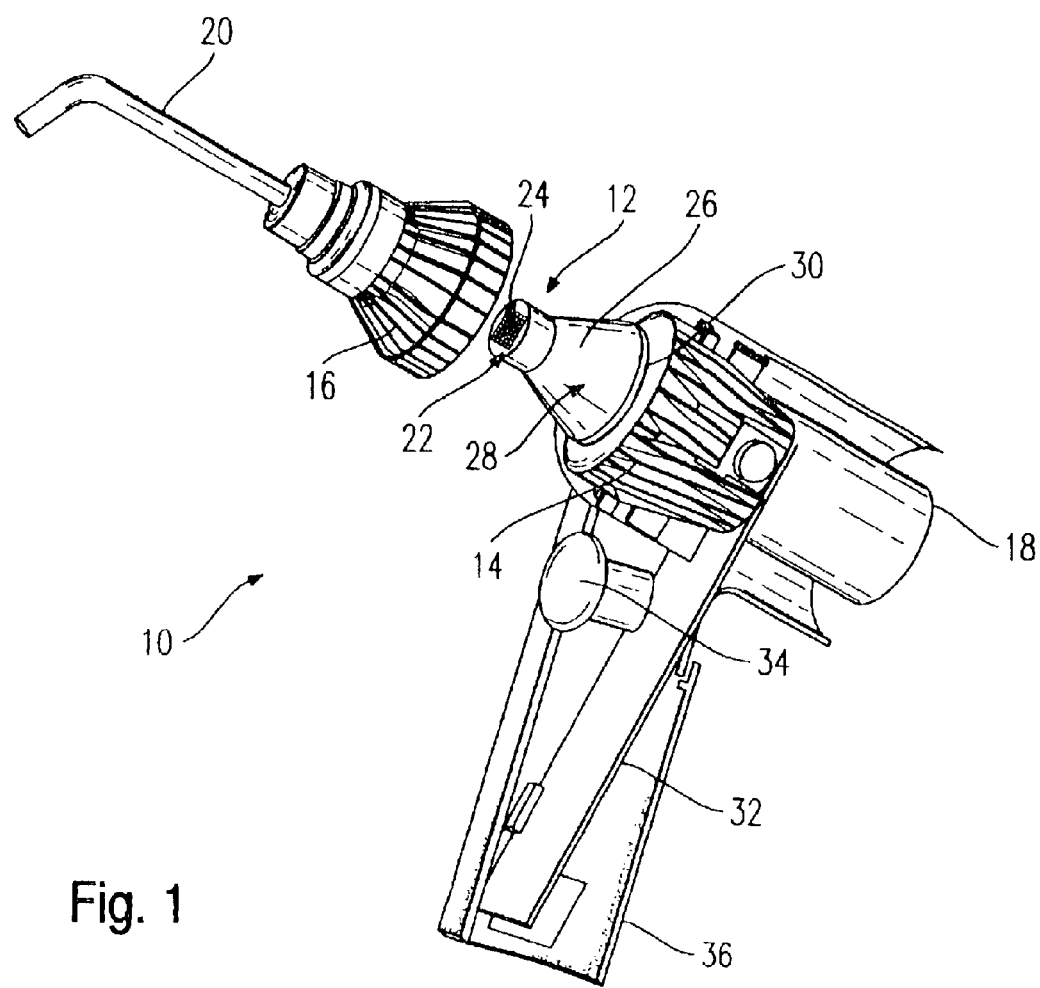
FIG. 1 is a schematic side view of one embodiment of the light hardening device of the present invention, whereby one-half of the housing and the counter ribbed element body thereof have been omitted; and, FIG. 2 is an enlarged perspective view of the light source of the present invention suitable for disposition in the one embodiment of the light hardening device of the present invention shown in FIG. 1.

As seen in FIG. 1, a light hardening device 10 includes a light source 12 which is mounted between a ribbed element body 14 and a counter ribbed element body 16. In the depiction of the embodiment of the light hardening device shown in FIG. 1, the counter ribbed element body has been detached.

The two ribbed element bodies include lengthwise or longitudinal ribs arranged in a one over another aligned arrangement so that the air conducted in an air path from the front toward the rear cools the ribs. In this connection, a forced air element is provided as a cooling element 18 which is arranged behind the ribbed element 14.

The counter ribbed element body 16 includes a connection for a light guide element 20 which extends, in a conventional manner, in a forward direction toward the light guide rod. An LED arrangement 22 is disposed immediately adjacent the entry of the light guide element 20 on a rear surface 24 of a cooling body 26. The disposal or mounting of the LED chips in a conventional manner by, for example, silver brazing or the like, leads to a good heat conducting connection. The rear surface 24 has a cross-section which is merely somewhat greater than the cross-section of the light guide rod and, in any event, is substantially smaller than the maximum cross-section of the cooling body 26 by, for example, a factor of 5 to 10.

The cooling body 24 is, in the embodiment illustrated in FIG. 1, configured substantially conically and includes a sleeve surface 28 whose configuration is accommodated to, or corresponds to, the configuration or geometry of the inner surface of the counter ribbed element body 16.

From a region of the maximum diameter 30 of the cooling body 26, the cooling body extends rearwardly within the ribbed element body 14 although this is not shown in FIG. 1. From there, the cooling body 26 extends in a conical or spherical manner and includes a configuration or shape which corresponds to that of the outer configuration of a commercially available halogen glow lamp. This form is chosen such that this geometry offers a minimal resistance to heat transfer relative to the ribbed element body 14.

Figure 3:
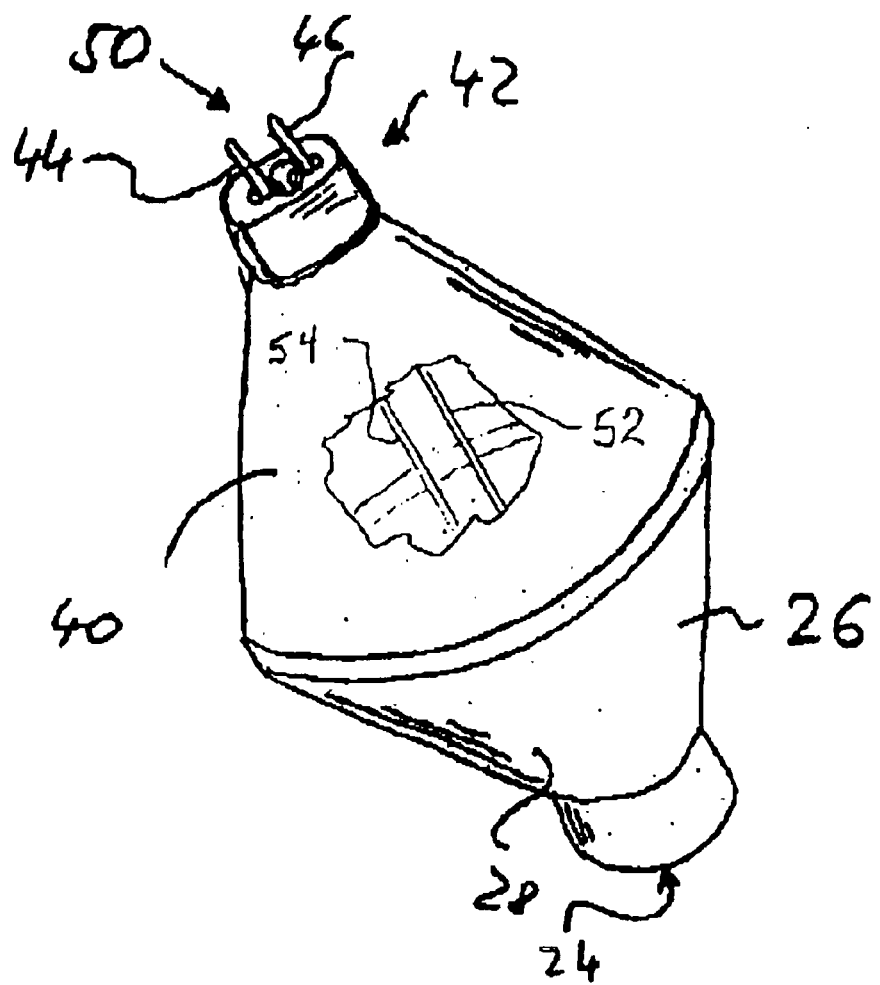
FIG. 3 shows a cooling body for a light hardening device, the cooling body including passages through which extend a plurality of connections which connect the two plug elements on the side of the cooling body disposed in opposition to the light source, a portion of the structure being broken away to better illustrate the connections.

FIG. 3 shows die cooling body 26. The LED arrangement 22 is disposed on a rear surface 24 of the cooling body. The cooling body has a conical shaped sleeve surface 28 and another conical shaped sleeve surface 40 as can be seen from FIG. 3. The conical shaped sleeves 28, 40 are each made in one piece and may be formed from any suitable material, for example—aluminum. The conical sleeve surface 40 terminates in two plug elements 44,46 or insertion rods, and which corresponds to the plug elements of a reflecting halogen glow lamp of the type shown in U.S. Pat. No. 6,123,545. A passage 50 runs through the cooling body 26, receiving two wires 52, 54 for electrical connection of the LED arrangement 22 arranged on the rear surface 24 with the two plug elements 44,46. By this approach, the connecting wires 52, 54 extend in an insulated manner through the cooling body 26, 40 and it is possible to provide the LED arrangement 22 with the stored voltage normally provided for a halogen glow lamp.

The light hardening device 10 otherwise includes conventional components such as, for example, an electronic circuit board 32 which serves as the socket connection for electrically connecting the light source 12 and, at the same time, serves as a mounting location for a push button panel 34. The light hardening device 10 further includes a conventional pistol-shaped housing 36.

Figure 2:
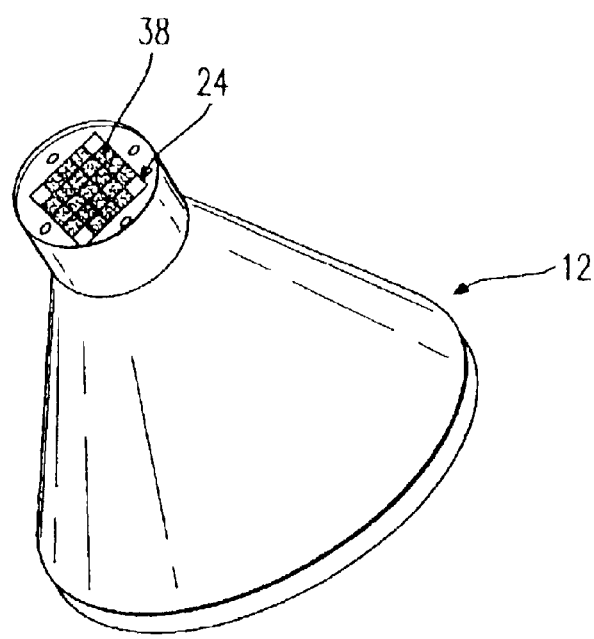

As seen in FIG. 2, a light source 12 of the present invention is illustrated in enlarged perspective view. The light source includes on its rear surface 24 an arrangement of 21 LED chips 38 which are arranged in close packed disposition to one another. The light emitting cross-section is in an arcuate form and is configured in this manner by omission of the corner chips so that a reflection free guiding of the emitted light into the light guide element 20 is possible.

Although a plurality of 21 of the chips 38 is shown, preferably, the arrangement is comprised of 32 chips in a 6×6 arrangement without, however, the provision of the corner chips. In this manner, a particularly high light output or performance is achieved and the electrical capacity of a typical light hardening device is better exploited in comparison with that of a 50 watt halogen glow lamp. With a forward voltage of 3 volts per chip, groups comprised each of 4 chips in a row can be actuated so that 8 parallel actuated chip groups are available.

As required, different LED chips can be mounted whereby an integrated control device can be disposed in the cooling body for selected actuation of the chip groups.

The specification incorporates by reference the disclosure of German priority document P 101 27 416.5.

It is a further feature of this invention that the LED arrangement, including the cooling body, is configured for a storage voltage of between 10 and 14 volts and is configured for deployment in lieu of a reflecting halogen glow lamp.

The LED arrangement emits light in the spectral region between 350 and 600 nanometers and, especially, is provided with a plurality of LEDs which emit light at an emission maximum in the range of short wave lengths and emit light at a further emission maximum at a longer wave length.

The light source has a light output of more than 400 milliwatts per square centimeter, preferably, 800 milliwatts per square centimeter and, especially preferably, approximately 1,000 milliwatts per square centimeter.

The cooling body is operable to receive an impulse/pause transmitter which is operable intermittently control the LED arrangement.

The cooling body, including the LED arrangement is disposable in a tension fit mounting in a combination comprised of a ribbed element body and a counter ribbed element body which are connected to one another and, especially, are connected to one another by threaded means.

A plurality of LEDs are arranged on the rear surface of the cooling body in matrix form whereby the LEDs are disposed parallel to one another and in rows for creating an operational voltage between 10 and 14 volts and the LEDs substantially fill our the rear surface.

What is claimed is:

1. A light hardening device comprising:

a housing;

a light guide carried by the household;

a light source mounted within housing, the light source having a plurality of LEDs in direct neighboring relationship to the light guide, the LEDs being supplied by an electrical energy source; and a cooling mounted within the housing and arranged upstream of the light source and operable to cool the light hardening device, the LED arrangement being disposed on a rear surface of the cooling body and the light source having a connection in the manner of a halogen glow lamp.

2. A light hardening device according to claim 1, wherein the cooling body includes a substantially conically shaped part and the LED arrangement is disposed on the peak of the cone.

3. A light hardening device according to claim 1, wherein the cooling body includes a cooling element for circulating a cooling medium therearound.

4. A light hardening device according to claim 1, wherein the light emitted from the light source reaches the light guide element in a reflection free manner.

5. A light hardening device according to claim 1, wherein the housing includes a ribbed element body, the cooling body being disposed in heat transfer relation to the ribbed element body, the ribbed element body having cooling ribs disposed on its outer surface.

6. A light hardening device according to claim 1, wherein the cooling body is of a double conical configuration, conical portion being disposed away from the LED arrangement and being in a configuration substantially conforming to the exterior form of a reflecting halogen glow lamp.

7. A light hardening device according to claim 6, wherein the housing includes a ribbed element body, said conical portion of the cooling body disposed away from the LED arrangement being in heat transfer relation to a ribbed element body.

8. A light hardening device according to claim 1, wherein the cooling body comprises metal formed with a hollow interior.

9. A light hardening device according to claim 8, wherein the cooling body has two plug elements on the side of the cooling body disposed in opposition to the light source and which are configured for receipt in socket elements for a halogen glow lamp, the cooling a body further including passages for wires which extend from the two plug elements to the light source.

10. A light hardening device according to claim 1, wherein the housing carries a forced air device.

11. A light hardening device according to claim 1, whereby the LED arrangement including the cooling body is configured for a storage voltage of between 10 and 14 volts and is configured for deployment in lieu of a reflecting halogen glow lamp.

12. A light hardening device according to claim 1, wherein the LED arrangement emits light in the spectral region between 350 and 600 nanometers.

13. A light hardening device according to claim 1, wherein the light source has a light output of more than 400 milliwatts per square centimeter.

14. A light hardening device according to claim 1, wherein the cooling body is operable to receive an impulse/pause transmitter which is operable to intermittently control the LED arrangement.

15. A light hardening device according to claim 1, wherein the cooling body including the LED arrangement is disposable in a tension fit mounting in a combination comprised of a ribbed element body and a counter ribbed element body which are connected to one another.

16. A light hardening device according to claim 1, wherein a plurality of LEDs are arranged on the rear surface in matrix form whereby die LEDs are disposed parallel to one another and in rows for creating an operational voltage between 10 and 14 volts and the LEDS substantially fill out the rear surface.

17. A light source comprising:
   a plurality of LEDs;
   a cooling body on which the LEDs are mounted, the cooling body being of a double conical configuration, the LEDs being mounted on the end of a first part of the double conical, the second part of the double conical configuration corresponding to the respective connector element and overall exterior geometry of a conventional reflecting halogen glow lump having a rated voltage of 12 volts.

18. A light source according to claim 17, wherein the light source is disposable in a housing light hardening device in lieu of a conventional reflecting halogen glow lamp for emitting light to effect the light hardening of a light hardenable mass.

19. A light hardening device according to claim 12 wherein the LED arrangement is provided with a plurality of LEDS which emit light at an emission maximum in the range of short wave lengths and emit light at a further emission maximum at a longer wave length.

* * * * *

UNITED STATES PATENT AND TRADEMARK OFFICE
CERTIFICATE OF CORRECTION

PATENT NO. : 6,767,109 B2
DATED : July 27, 2004
INVENTOR(S) : Wolfgang Plank et al.

It is certified that error appears in the above-identified patent and that said Letters Patent is hereby corrected as shown below:

Column 6,
Line 35, "household" should be -- housing --;
Line 36, -- the -- should be inserted before "housing";
Line 40, -- body -- should be inserted after "cooling";
Line 44, "a" (first occurrence) should be rewritten as -- plug elements which form a mechanical/electrical --;
Line 63, -- a -- should be inserted before "conical";

Column 7,
Line 11, "a" should be deleted;

Column 8,
Line 6, "die" should be changed to -- the --;
Line 8, "LEDS" should be changed to -- LEDs --;
Line 19, "lump" should be changed to -- lamp --
Lines 19-20, "a rated voltage of 12 volts" should be changed to -- plug elements which form a mechanincal/electrical connection --;
Line 22, -- of a -- should be inserted before "light"; and
Line 23, "LEDS" should be -- LEDs --.

Signed and Sealed this

Thirtieth Day of November, 2004

JON W. DUDAS
*Director of the United States Patent and Trademark Office*